United States Patent
Rifai

(10) Patent No.: US 8,721,844 B2
(45) Date of Patent: May 13, 2014

(54) DENTAL COMPOSITE CURING SYSTEM, APPARATUS, AND METHOD

(76) Inventor: Mohammad Al Rifai, Daraa (SY)

( * ) Notice: Subject to any disclaimer, the term of this patent is extended or adjusted under 35 U.S.C. 154(b) by 232 days.

(21) Appl. No.: 13/280,615

(22) Filed: Oct. 25, 2011

(65) Prior Publication Data

US 2012/0101182 A1    Apr. 26, 2012

Related U.S. Application Data

(60) Provisional application No. 61/406,557, filed on Oct. 25, 2010.

(51) Int. Cl.
    B01J 19/12    (2006.01)
    B01J 19/08    (2006.01)
    A61K 6/083    (2006.01)
    A61K 6/08     (2006.01)

(52) U.S. Cl.
    USPC ............ 204/157.63; 204/157.15; 204/157.44; 204/157.6; 433/29; 433/215; 433/222.1; 433/229; 427/510; 427/497; 427/517; 427/508; 522/908; 523/113; 523/115; 523/120; 250/493.1; 250/503.1; 250/504 R; 250/505.1; 250/515.1

(58) Field of Classification Search
    USPC ............ 204/157.15, 157.44, 157.63; 433/29; 433/215, 222.1, 229; 427/510, 487, 517, 427/508; 522/908; 523/113, 115, 120; 250/493.1, 503.1, 504 R, 505.1, 515.1
    See application file for complete search history.

(56) References Cited

U.S. PATENT DOCUMENTS

| | | | |
|---|---|---|---|
| 5,290,169 A | 3/1994 | Friedman et al. | |
| 5,468,577 A | 11/1995 | Bae | |
| 5,749,724 A | 5/1998 | Cheng | |
| 6,033,223 A | 3/2000 | Narusawa et al. | |
| 6,282,013 B1 | 8/2001 | Ostler et al. | |
| 6,350,122 B1 | 2/2002 | Meyer | |
| 6,482,004 B1 | 11/2002 | Senn et al. | |
| 6,602,074 B1 | 8/2003 | Suh et al. | |
| 6,783,810 B2 * | 8/2004 | Jin et al. | 427/510 |
| 6,855,197 B2 | 2/2005 | Su et al. | |
| 2002/0016378 A1 * | 2/2002 | Jin et al. | 522/1 |
| 2003/0222365 A1 | 12/2003 | Vogel et al. | |
| 2004/0162364 A1 | 8/2004 | Su et al. | |

FOREIGN PATENT DOCUMENTS

| | | |
|---|---|---|
| EP | 0875360 A2 | 11/1998 |
| JP | 2000166941 A * | 6/2000 |
| WO | WO0067048 A2 | 5/2000 |

* cited by examiner

*Primary Examiner* — Sanza McClendon
(74) *Attorney, Agent, or Firm* — Christopher Wood; Premier Law Group, PLLC

(57) ABSTRACT

Dental curing systems, apparatuses, and methods may include a light source, a perforated plate, and a dental composite. The perforated plate may be positioned between the light source and the dental composite. The perforated plate may include a plurality of perforations that convert a first curing light beam from the light source into multiple curing light beams before reaching the dental composite. The multiple curing light beams come in contact with the dental composite to begin the curing process at certain locations on the dental composite. The perforated plate may then be removed, and a second curing light beam from the light source may be applied to the dental composite to complete the curing process.

20 Claims, 9 Drawing Sheets

DENTAL COMPOSITE CURING SYSTEM, APPARATUS, AND METHOD

CROSS-REFERENCE TO RELATED APPLICATIONS

This application claims the benefit of priority from U.S. Provisional Patent Application Ser. No. 61/406,557 (filed Oct. 25, 2010). The entire content of Provisional Patent Application Ser. No. 61/406,557 is incorporated herein by reference in its entirety.

STATEMENT REGARDING FEDERALLY SPONSORED RESEARCH OR DEVELOPMENT

Not Applicable.

FIELD

The present invention generally relates to dental composite curing solutions.

BACKGROUND

Dental restoration techniques include the use of polymers and other restorative materials to regain a tooth's function, form, and integrity. In a restorative technique referred to as photopolymerization, a polymer adhesive is applied to a tooth or portion thereof. The adhesive is then exposed to a light of a certain wavelength, which causes a chemical reaction to occur between the polymers of the adhesive. This reaction transforms the adhesive from a liquid or pliable state to a solid state intended to withstand strains, pressures, and other conditions often experienced by teeth.

SUMMARY

In some embodiments of the present invention, a dental curing method may include positioning a perforated plate between a light source and a dental composite. The perforated plate may have a plurality of perforations configured to convert a curing light beam into multiple curing light beams. The method may also include projecting a first curing light beam from the light source toward the perforated plate to simultaneously expose the dental composite to multiple curing light beams. The method may further include removing the perforated plate and projecting a second curing light beam toward the dental composite for additional curing.

In certain embodiments, the positioning of the perforated plate may include removably securing the perforated plate with one or more plate securement members. In other embodiments, the positioning of the perforated plate may include positioning the perforated plate using a plate placement member connected to the perforated plate.

In some embodiments, the plurality of perforations may include evenly spaced and circular-shaped through-holes. In such embodiments, the through-holes may be approximately 1 millimeter (mm) in diameter and spatially separated from other through-holes by approximately 1 mm. In certain embodiments, the method may also include exposing the dental composite to the multiple curing light beams until light-exposed portions of the dental composite are at least partially cured.

In other embodiments of the present invention, a dental curing apparatus includes a perforated plate positioned between a light source and a dental composite. The perforated plate may include a plurality of perforations configured to convert a curing light beam from the light source into multiple curing light beams.

In certain embodiments, the dental curing apparatus includes one or more plate securement members configured to removably secure the perforated plate between the light source and the dental composite. In such embodiments, the plate securement members may include two inwardly biased springs positioned along opposite sides of the perforated plate. In other embodiments, the dental curing apparatus may include a plate placement member connected to the perforated plate. In some embodiments, the plurality of perforations may include evenly spaced and circular-shaped through-holes. In such embodiments, each of the through-holes may be approximately 1 mm in diameter and spatially separated from other through-holes by approximately 1 mm.

In yet other embodiments of the present invention, a dental curing system may include a light source configured to produce a curing light beam and a perforated plate positioned between the light source and a dental composite. The perforated plate may include a plurality of perforations configured to convert the curing light beam into multiple curing light beams.

In certain embodiments, the dental curing system may also include plate securement members configured to removably secure the perforated plate between the light source and the dental composite. In such embodiments, the plate securement members may be inwardly biased springs positioned along opposite sides of the perforated plate. In other embodiments, the dental curing system may include a plate placement member connected to the perforated plate. In some embodiments, the plurality of perforations may include evenly spaced and circular-shaped through-holes. In such embodiments, the through-holes may each be approximately 1 mm in diameter and spatially separated from one another by approximately 1 mm.

BRIEF DESCRIPTION OF THE DRAWINGS

A more particular description of the present invention will now be rendered by reference to the appended Figures. These Figures depict only some embodiments of the invention and are not limiting of its scope. Regarding the Figures.

DETAILED DESCRIPTION

The present invention has been developed in response to the present state of the art, and in particular, in response to problems and needs that have not yet been adequately recognized and/or resolved by currently available technologies.

As discussed above, currently available dental restoration techniques include applying a pliable adhesive or composite to a tooth, and exposing the composite to a light of a given wavelength. However, while such techniques are effective to some extent, they have significant limitations. For instance, currently available techniques can frequently cause the composite to undergo significant shrinkage during a curing or polymerization process, which can significantly limit or compromise the effectiveness of the dental restoration procedure.

Accordingly, among the benefits and embodiments of the present invention are solutions to such limitations. Indeed, certain embodiments of the present invention include systems, apparatuses, and methods for curing dental composites without composite shrinkage. Stated another way, embodiments of the present invention provide dental restorative solutions that produce superior fillings, crowns, and other dental restorative structures.

The description and Figures presented herein demonstrate that the present invention may be practiced or implemented in a variety of embodiments. The discussion of these embodiments amounts to a complete written description that enables those of ordinary skill in the art to make and use the invention. While several embodiments are expressly disclosed herein, it should be appreciated that the present invention is not limited to the specifically disclosed embodiments. Indeed, the structures, features, operations or functions of the described embodiments may be reorganized or reconfigured to create one or more embodiments that are not specifically discussed herein, but nevertheless fall within the scope the present invention.

Further, the use of words or phrases such as "certain embodiments," "some embodiments," "may," "can," or similar language means that a particular feature, structure, function, characteristic, or benefit described in connection with an embodiment is included in at least one embodiment of the present invention. Thus, appearances of "certain embodiments," "some embodiments," "may," "can," or similar language do not necessarily all refer to the same embodiment or group of embodiments, and the described features, structures, functions, characteristics, or benefits may vary from one embodiment to another.

Figure 1:
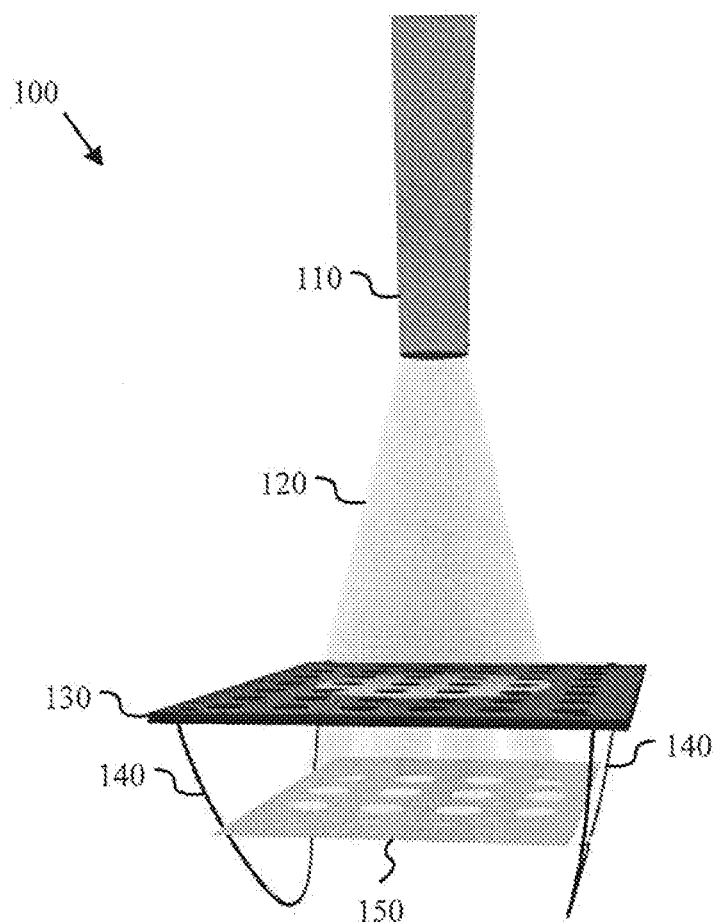
FIG. 1 is a perspective view of a dental composite curing system in accordance with one or more embodiments of the present invention.

FIG. 1 is a perspective view of a dental composite curing system 100 in accordance with one or more embodiments of the present invention. The depicted system 100 includes a light source 110, a curing light beam 120, a perforated plate 130, plate securement members 140, and a dental composite surface 150. In certain embodiments, the system 100 provides a dental restorative solution that is capable of producing superior fillings, crowns, and other dental restorative structures by eliminating or significantly reducing dental composite shrinkage.

As depicted, the light source 110 may be configured to produce or otherwise emit the curing light beam 120 that comes in contact with the perforated plate 130. The perforated plate 130 may be connected to plate securement members 140 that can be used to removably secure the perforated plate 130 in an appropriate position between the light source 110 and the dental composite 150. Additionally, the perforated plate 130 may include a plurality of perforations or through-holes that can convert the curing light beam 120 into multiple curing light beams before coming in contact with the dental composite 150.

Since polymerization only occurs in the light-exposed areas of the dental composite 150, dividing a curing light beam in this manner can isolate composite shrinkage to certain areas, which, in turn, causes the remaining areas of the dental composite 150 to compensate by expanding. With the overall dental composite 150 in such a condition, the amount of shrinkage that later result from finishing the curing process by removing the perforated plate 130 and projecting a second curing light beam onto the dental composite 150 is minimal. Accordingly, embodiments of the dental composite curing system 100 are capable of producing superior fillings, crowns, and other dental restorative structures by initially curing, or partially curing, only certain portions of the dental composite 150. In certain embodiments, the form of the perforations or holes can be chosen in the shape of circles because, when the light passes and cures the areas under the holes, the cured areas can be in shapes of cylinders; in this way, stress point formation can be avoided.

Figure 2:
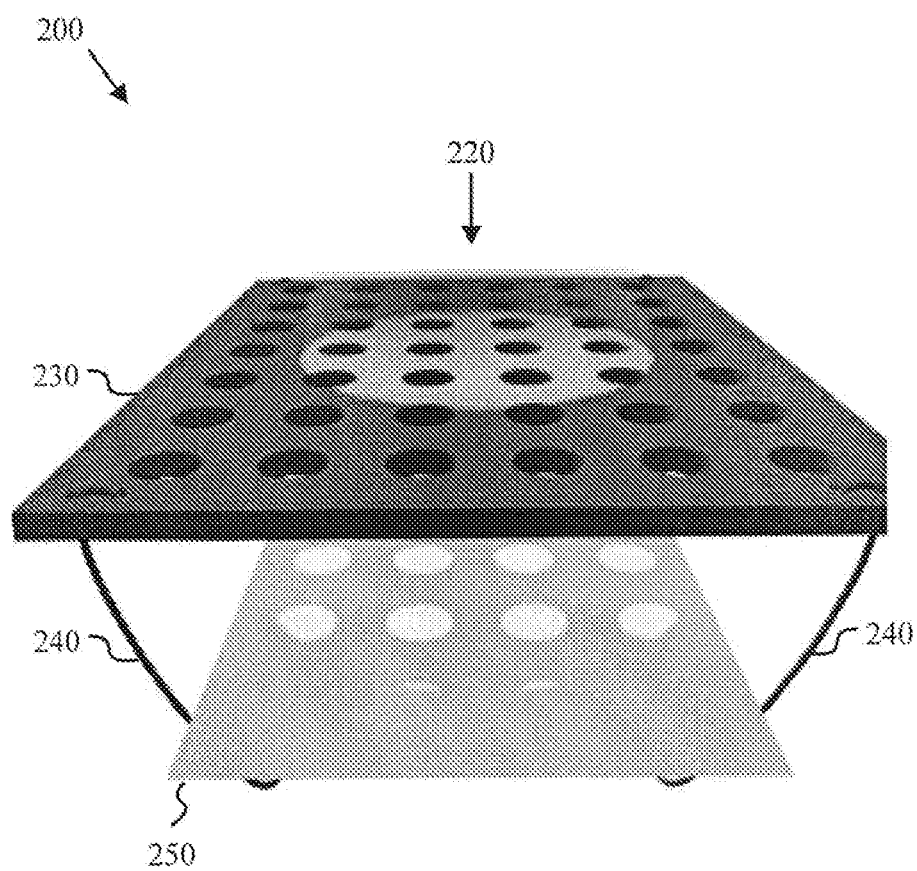
FIG. 2 is a perspective view of a dental composite curing apparatus in accordance with one or more embodiments of the present invention.

FIG. 2 is a perspective view of a dental composite curing apparatus 200 in accordance with one or more embodiments of the present invention. The depicted apparatus 200 includes a curing light beam 220, a perforated plate 230, plate securement members 240, and a dental composite 250. In certain embodiments, the dental composite curing apparatus 200 corresponds to one or more of the embodiments discussed elsewhere in this specification.

The perforated plate 230 may include a plurality of perforations or through-holes capable of permitting light to pass therethrough. In certain embodiments, the through-holes may be substantially circular in shape, as depicted. In addition, the through-holes may be approximately 1 mm in diameter and located approximately 1 mm away from one another. However, the perforations or through-holes in other embodiments may vary greatly in size, shape, and distance, depending upon the embodiment. In certain embodiments, using conic shapes for the perforations on the perforated plate 230 can minimize and even eliminate the formation of stress points on the dental composite 250.

In certain embodiments, the perforated plate 230 may consist or be formed from a variety of partially or completely opaque materials, including readily available materials such as stainless steel. In addition, the perforated plate 230 may be attached or otherwise mechanically connected to one or more plate securement members 240. In certain embodiments, the plate may be fixed on the targeted tooth with a minimal amount of distance from the composite surface. In such embodiments, even if the doctor's or dentist's hand shakes during the curing process, the shaking may not significantly affect the path of the light. In some embodiments, the dental composite 250 may be embodied by a variety of restorative composites. For instance, the dental composite 250 may include any number of photopolymerizable coatings, compositions, or resins.

Figure 3:
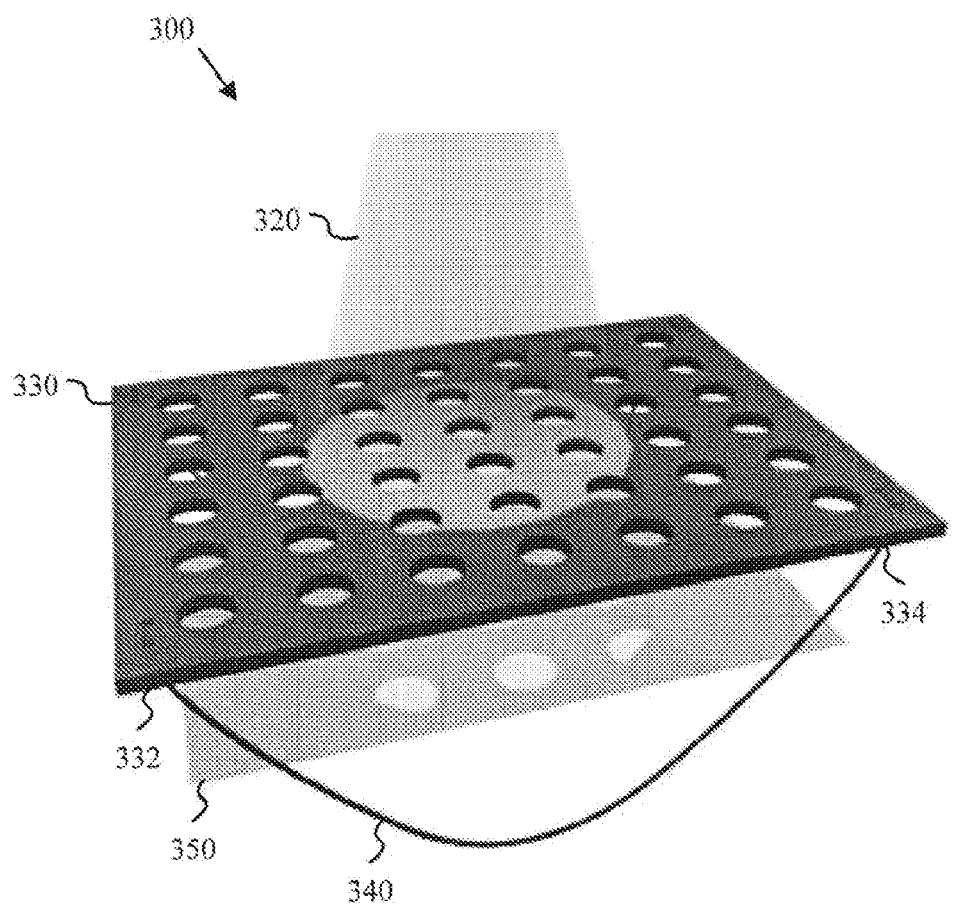
FIG. 3 is a side perspective view of a dental composite curing apparatus in accordance with one or more embodiments of the present invention.

FIG. 3 is a side perspective view of a dental composite curing apparatus 300 in accordance with one or more embodiments of the present invention. The depicted apparatus 300 includes a curing light beam 320, a perforated plate 330, a plate securement member 340, and a dental composite 350. In certain embodiments, the dental composite curing apparatus 300 may correspond to one or more embodiments discussed elsewhere in this specification.

As discussed above, the plate securement member 340 may be configured to removably secure the perforated plate 330 in a suitable position between the curing light beam source (not shown) and the dental composite 350. Also, since FIG. 3 is a side perspective view, the depicted dental composite curing apparatus 300 may appear at first glance to only have one plate securement member 340, which is secured to the perforated plate 330 at corners 332 and 334.

However, comparing FIG. 3 with FIGS. 1-2, it should be appreciated that embodiments of the present invention may include two plate securement members along opposite sides of a perforated plate (see, for example, FIG. 1). In such embodiments, the plate securement members may be springs that are biased toward one another, thereby creating a pinching force that may engage a tooth or other oral feature and removably secure the perforated plate 330 in an appropriate position. In such embodiments, the springs or securement members may be positioned to correspond respectively to a vestibular side and a lingual side of a tooth or other oral feature of a patient.

Figure 4:
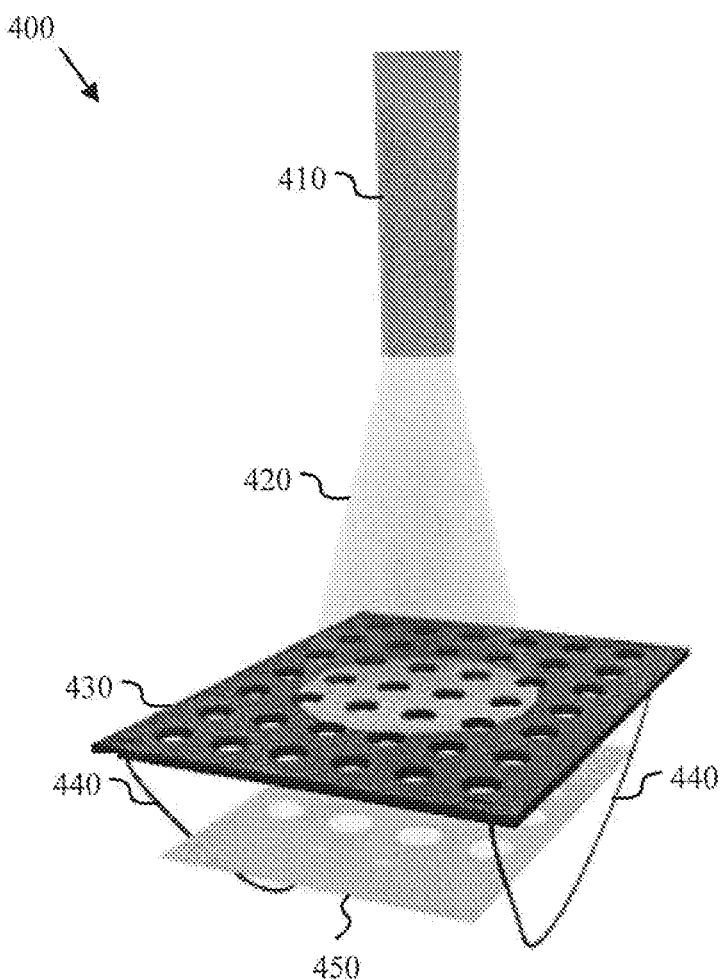
FIG. 4 is a perspective view of another dental composite curing system in accordance with one or more embodiments of the present invention.

FIG. 4 is a perspective view of another dental composite curing system 400 in accordance with one or more embodiments of the present invention. The depicted system 400 includes a light source 410, a curing light beam 420, a perforated plate 430, plate securement members 440, and a dental composite 450. In certain embodiments, the composite curing system 400 may correspond to one or more embodiments discussed throughout this specification.

The light source 410 may include any variety of devices capable of producing a light beam fit for curing one or more dental composites 450. In some embodiments, the light source 410 is configured to produce a curing light beam 420 at a preselected wavelength. For instance, in certain embodiments, the light source 410 is configured to produce a blue light with a wavelength of approximately 650 nanometers (nm).

In addition, depending on the embodiment, the light source 410 may be configured to produce a curing light beam 420 with distinct dimensions. For instance, in the depicted embodiment, when the curing light beam 420 comes in contact with the perforated plate 430, the curing light beam 420 creates a substantially circular pattern. However, the light source 410 may be configured to produce a curing light beam 420 with dimensions that create an oval, triangular, or rectangular pattern on the perforated plate 430. Similarly, the vertical distance between the light source 410 and the perforated plate 430 may vary from one embodiment to another. As such, a curing light beam 420 may include any type, quantity, or intensity of light sufficient to induce the dental composite to undergo a photopolymerization or curing reaction.

Figure 5A:
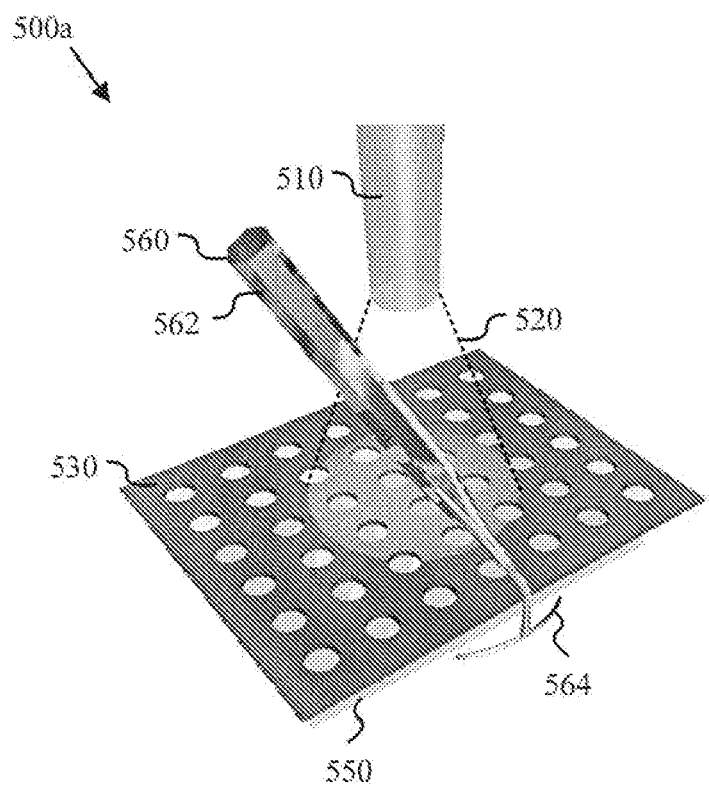
FIGS. 5a-5b show are perspective views of another dental composite curing apparatus in accordance with one or more embodiments of the present invention.
Figure 5B:
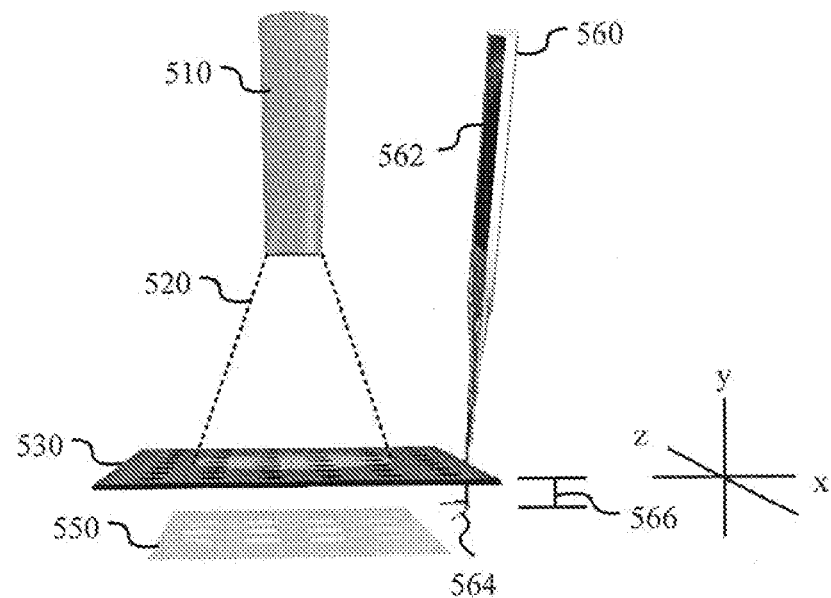

FIGS. 5a-5b are perspective views of another dental composite curing apparatus in accordance with one or more embodiments of the present invention. Similar to some of the embodiments discussed above, the dental composite curing systems of FIGS. 5a-5b include a curing light source 510, a curing light beam 520, a perforated plate 530, and a dental composite surface 550. However, unlike some of the embodiments discussed above, the systems of FIGS. 5a-5b do not include plate securement members (see, for example, the plate securement members 140 of FIG. 1).

Instead, the systems of FIGS. 5a-5b include a plate placement member 560 that is attached to the perforated plate 530. As depicted, the plate placement member 560 may include a handle portion 562 and an arching portion 564. As such, a doctor or dentist may, for example, position and control the perforated plate 530 by grasping the handle portion 562 of the plate placement member 560 and resting or otherwise engaging the arching portion 564 on the vestibular or lingual side of a targeted tooth (not shown). In certain embodiments, the increased control that can result from embodiments with the plate placement member 560 can provide increased stability, accuracy, and quality regarding the overall dental restoration procedure.

In certain embodiments, the features of the plate placement member 560 may vary from the depicted embodiment. For instance, in certain embodiments, the vertical distance 566 between the perforated plate 530 and the arching portion 564 may be preselected to minimize the negative effects that a doctor's shaking hand might have the restoration procedure. In addition, the physical properties and dimensions of the arching portion 564 may vary according to the size and/or characteristics of the underlying tooth or other oral feature.

The physical characteristics of the handle portion may also vary. For instance, in certain embodiments, the handle portion 562 may be fashioned in a more ergonomically pleasing manner. In addition, the angle or pitch at which the plate placement member 560 relates to the perforated plate may vary along any or all of an x, y, or z axis. In fact, in certain embodiments, the angle or pitch may even be adjustable in order to provide additional advantages, such as being adaptable to a patient's ability to open his or her mouth or perhaps the physical location of a particular tooth or other oral feature.

Further, while the plate placement member 560 is depicted as being permanently affixed to the perforated plate 530, this may not be the case in all embodiments. For instance, in some embodiments, the plate placement member 560 may be removably secured to the perforated plate 530. This may be achieved by any number of additional features, including features that use one or more springs, clamps, ties, magnets, screws, or other mechanisms capable of removably securing the plate placement member 560 to the perforated plate 530.

Figure 6:
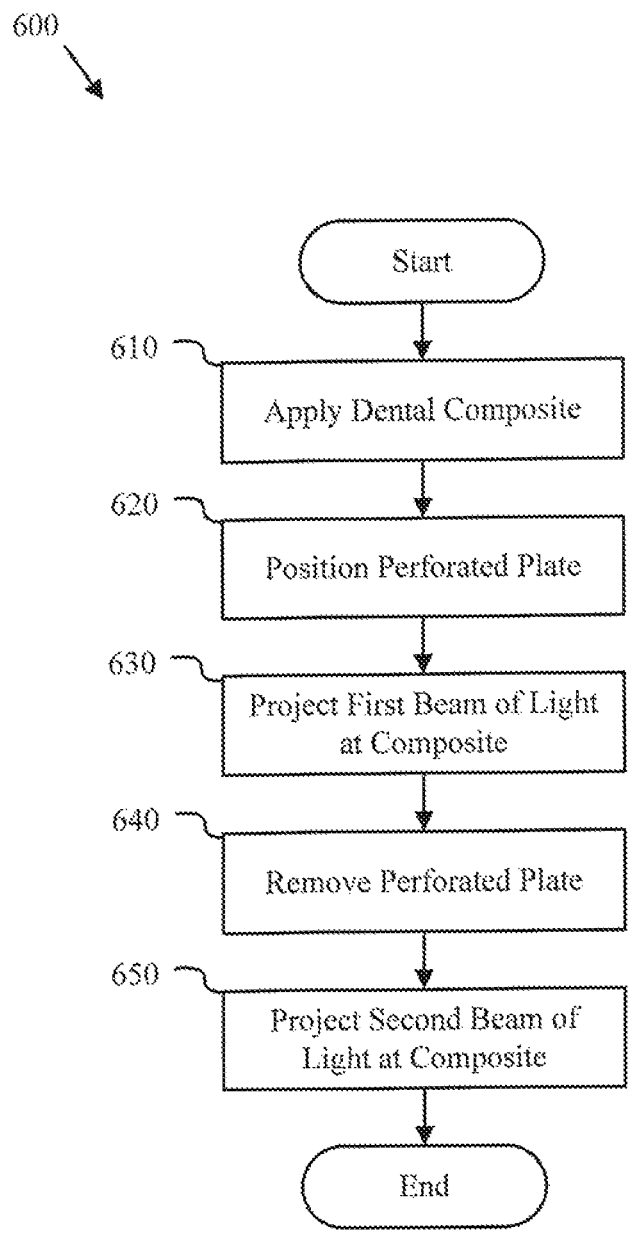
FIG. 6 is a flow chart diagram of a dental composite curing method in accordance with one or more embodiments of the present invention.

FIG. 6 is a flow chart diagram of a dental composite curing method 600 in accordance with one or more embodiments of the present invention. The method 600 includes applying 610 a dental composite, positioning 620 a perforated plate, projecting 630 a first curing light beam at the composite, removing 640 the perforated plate, and projecting 650 a second curing light beam at the composite, wherein the first and second curing light beams can be from the same curing light source. In certain embodiments, the method 600 may correspond to one or more embodiments discussed elsewhere in this specification.

The method 600 begins with applying 610 a dental composite. This may include painting or otherwise introducing one or more dental composites to a given location in a patient's mouth, such as a tooth. Once the dental composite has been adequately applied 610, a perforated plate may be positioned 620 at a suitable location above or otherwise covering the dental composite. In certain embodiments, the perforated plate may be removably secured in this position using plate securement members. In other embodiments, the perforated plate may be removably secured in this position using a plate placement member.

A first curing light beam may then be projected 630 at the dental composite. However, since the perforated plate is positioned 620 over the dental composite, the first curing light beam is converted into multiple curing light beams before the light beam arrives at the composite. After an appropriate amount of time has passed (e.g., perhaps 5-10 seconds), the perforated plate may be removed 640, and a second curing light beam may be projected 650 toward the dental composite to complete the curing process.

It should be appreciated that embodiments of the present invention can save time and effort by enabling a dentist to, for example, restore a class I cavity, with depths between 2-3 millimeters, in a single restorative step. Indeed, embodiments of the present invention can enable a dentist to fill an entire cavity, groove and form a corresponding surface, then proceed with polymerization by using a perforated plate for forty (40) seconds, removing the plate, and then applying a curing process for another forty (40) seconds. Accordingly, embodiments of the present invention can not only produce superior fillings, crowns, or other dental restorative structures, but embodiments of the present invention can also save on the time and effort that would otherwise be required by a given restorative procedure.

Figure 7:
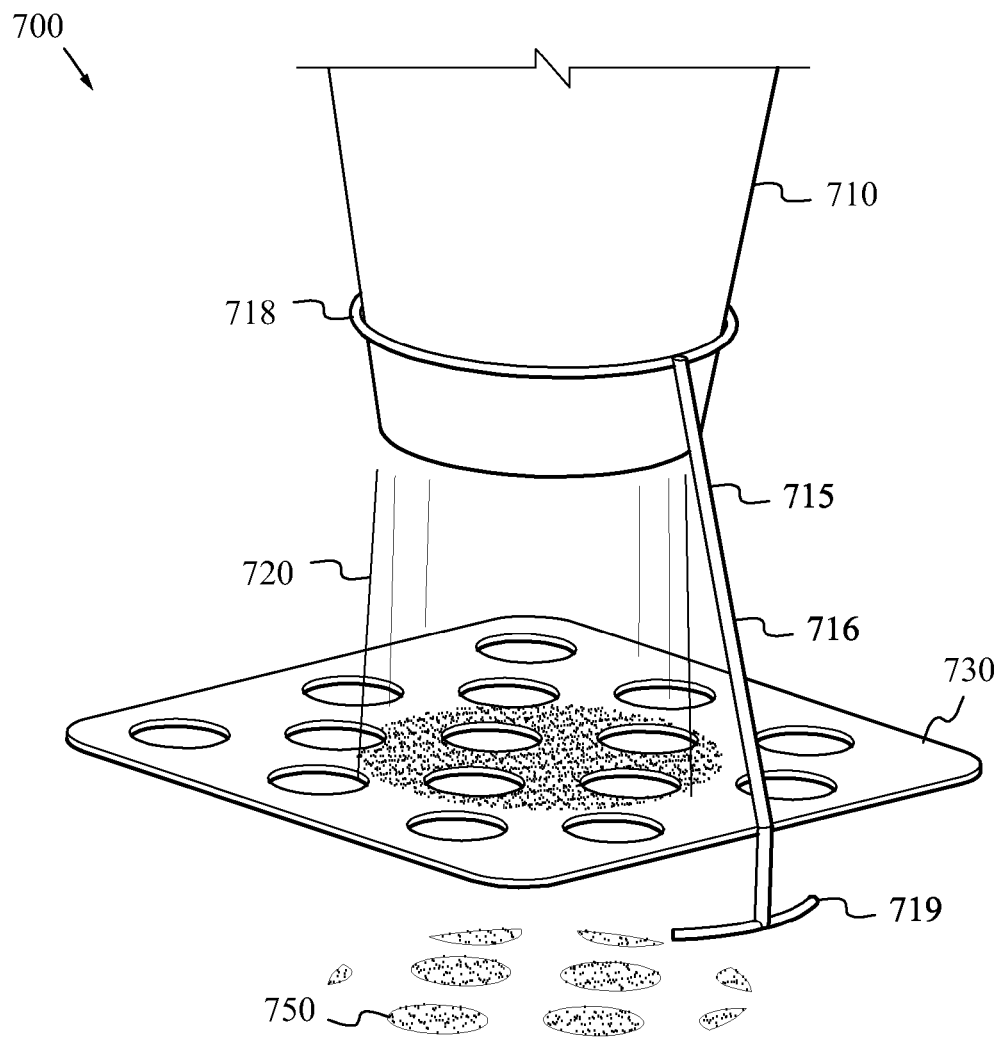
FIGS. 7-9 show perspective views of another dental composite curing apparatus in accordance with one or more embodiments of the present invention.
Figure 8:
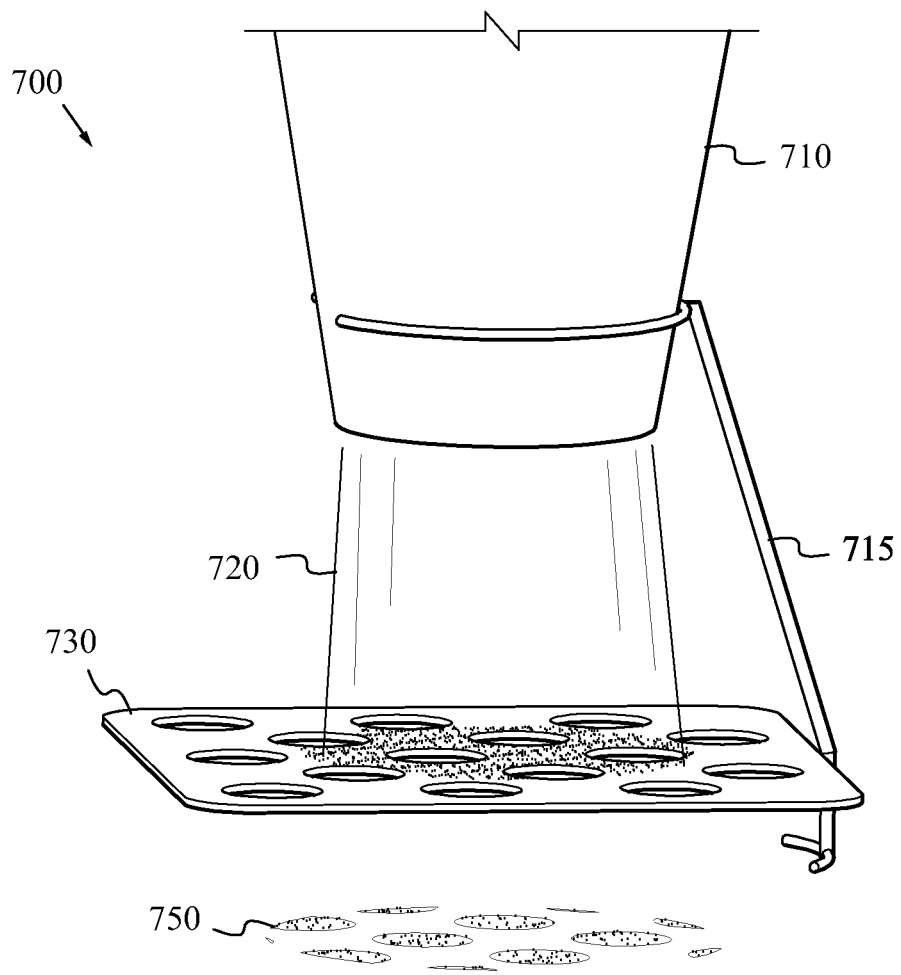
Figure 9:
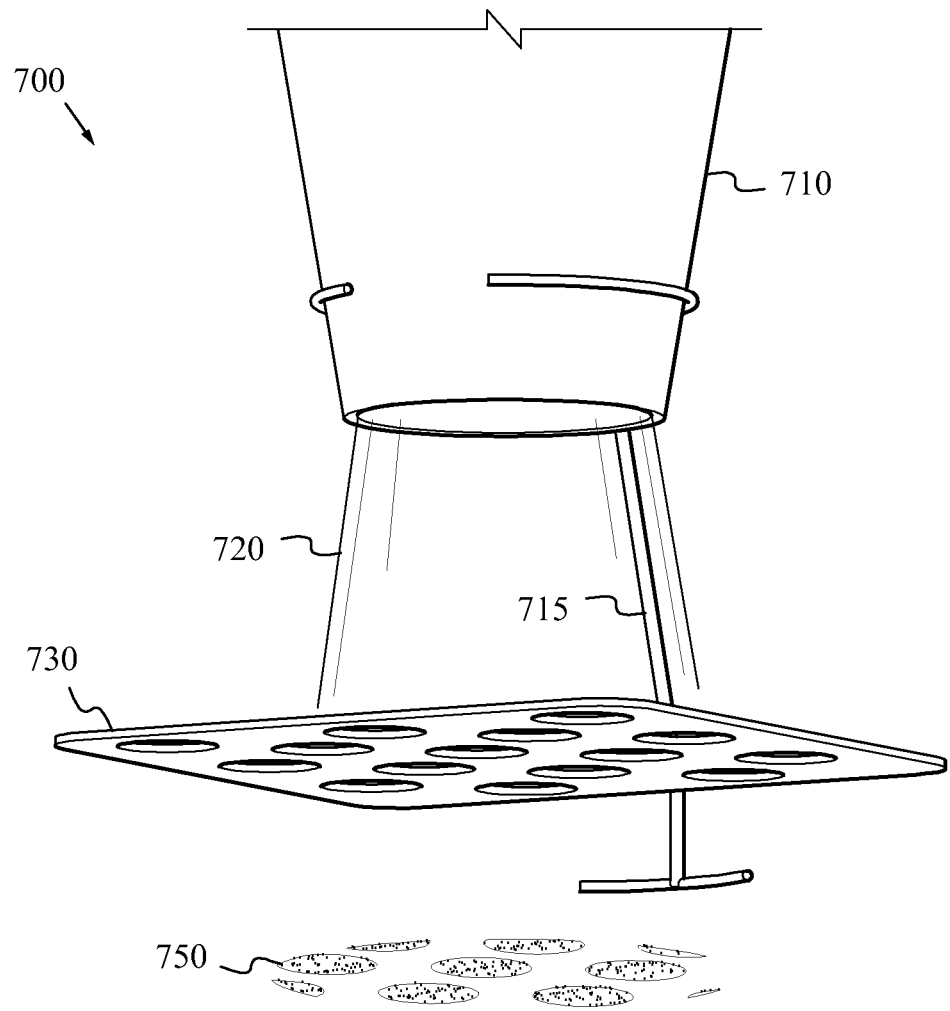

FIGS. 7 through 9 show views of a dental composite curing system 700 in accordance with one or more embodiments of the present invention. The depicted system 100 includes a light source 710, a holder 715, a perforated plate 730, and a dental composite surface 750. The light source provides a curing light beam 720. The holder 715 is made up of a middle portion in the form of an elongated arm 716 with a light source holder portion 718 and a rest portion 719 at opposite upper and bottom ends respectively of the elongated arm 716 of holder 715. The rest portion 719 can adopt any suitable shape such as a curved T-shaped as shown, for example, in FIG. 7.

The rest portion 719 of the holder 715 rests on the lingual or buccal surface during normal use of the dental composite curing system 700. One side of the perforated plate 730 is attached to the elongated arm 716 such that the holder 715 and perforated plate 730 form a single integral piece. During normal operation the curing light source 710 is supported by the light source holder portion 718 of holder 715. The light source holder portion 718 can take the form of a flexible ring and function somewhat like an automobile cup holder but instead of holding a cup or beverage the light source holder portion 718 is used to hold the light source 710.

In certain embodiments, the composites may shrink during polymerization, and the percentage of the shrinkage in some higher-end composites is approximately 1.5%. In certain embodiments, the plate of the described invention can divide the composite to polymerized and non-polymerized areas. So, this plate can decrease the amount of shrinkage within the composite because the shrinkage often depends on the size and shape of the composite restoration. In such a setting, the non-polymerized areas may slightly expand to compensate for the shrinkage of the polymerized areas, which can result in reduced shrinkage and stress formation.

In some embodiments, the present invention can enable the restoration of class one cavities (e.g., cavities with a depth of between 2-3 millimeters) in a single step. This can be done by using the plate described herein for approximately 40 seconds, but sometimes between 5-10 seconds, then removing the plate, and applying the curing process again for approximately 40 seconds. This can save time, effort, and almost eliminate shrinkage and stress composition.

In one study, the inventor sought to find the best combination that allows the highest number possible of perforations and achieve the highest number of both cured and non cured areas in the composite restoration (i.e., the smallest size of perforations and the smallest distance separating between perforations). Several combinations were studied for both perforation size and separating distance, and found the following:

I. Perforations of 0.5 mm, did not allow sufficient amount of curing light to pass through the perforated plate and thus was not able to cause the desired curing effect on the composite.

II. Perforations of 1 mm, allowed enough amount of curing light to pass through the perforated plate (I recorded 400 mW/cm$^2$ out of a source of 1100 mW/cm$^2$) and was able to cause the desired curing process in the composite. (Where "mW" is the unit for milliwatt).

III. Perforations of more than 1 mm was not desirable, mainly for two reasons
   1—It will reduce the number of perforations possible which contradicts with the general concept.
   2—In dental practice there are restorations of 1.5-2 mm in size, which means that a perforation of 1.5 mm or 2 mm in diameter has the potential of covering the whole surface of the restoration and cause the curing in the whole restoration which is what we are essentially trying to avoid.

IV. Perforations of 1 mm and 0.5 mm apart. I found that the light beams passing through the perforated plate (the plate must not exceed 0.5 mm in thickness to reduce the diminishing of curing light power) have almost reunited on the restoration surface after passing through the plate (due to the conic pattern of the light beams passing through the plate) and caused the curing affect on almost the whole restoration surface.

V. Perforations of 1 mm and 1 mm apart. This combination allowed for enough light power to pass through with suitable separations, and achieved the desired result of both cured and non cured areas of the composite restoration.

VI. Perforations of 1 mm and 1.5-2 mm apart were not suitable for reasons very similar to the reasons that lead to the rejection of 1.5-2 mm perforations above.

The above study found a plate of comprising 1 mm perforations and 1 mm apart to be the best combination that allows for enough curing light power to pass through the perforated plate, and achieve the desired focal curing process. The perforations can be in the range 0.8 mm to 1.2 mm inclusively, and their distance apart in the range 0.8 mm to 1.2 mm inclusively though it is preferred that the plate is made up of 1 mm perforations 1 mm apart.

It should be appreciated that the embodiments of the present invention are not limited to those specifically described above. For instance, the present invention may include different structures, features, or characteristics than those described above. Similarly, methods of making and using the present invention, as described herein, may include different operations, steps, or sequences than those described above. Therefore, it is to be understood that the present invention is not limited to the embodiments described above, but encompasses any and all embodiments within the scope of the following claims.

What is claimed:

1. A dental curing method, comprising:
   positioning a perforated plate between a light source and a dental composite, wherein the perforated plate comprises a plurality of perforations configured to convert a curing light beam into multiple curing light beams, further wherein the diameter of the perforations is in the range 0.8 millimeters to 1.2 millimeters inclusively, and their distance apart in the range 0.8 millimeters to 1.2 millimeters inclusively;
   projecting a first curing light beam from the light source toward the perforated plate to simultaneously expose the dental composite to multiple curing light beams;
   removing the perforated plate; and
   projecting a second curing light beam from the light source toward the dental composite for additional curing.

2. The dental curing method of claim 1, wherein the positioning of the perforated plate comprises removably securing the perforated plate using at least one plate securement member.

3. The dental curing method of claim 1, wherein the positioning of the perforated plate comprises positioning the perforated plate using a plate placement member connected to the perforated plate.

4. The dental curing method of claim 1, wherein the plurality of perforations comprises a plurality of evenly spaced and circular-shaped through-holes.

5. The dental curing method of claim 4, wherein each of the plurality of through-holes is 1 millimeter in diameter and spatially separated from other through-holes by 1 millimeter.

6. The dental curing method of claim 1, wherein projecting a first curing light beam from the light source toward the perforated plate comprises exposing the dental composite to the multiple curing light beams until light-exposed portions of the dental composite are at least partially cured.

7. A dental curing apparatus, comprising:
a perforated plate positioned between a light source and a dental composite, the perforated plate comprising a plurality of perforations configured to convert a curing light beam from the light source into multiple curing light beams before reaching the dental composite, wherein the diameter of the perforations is in the range 0.8 millimeters to 1.2 millimeters inclusively, and their distance apart in the range 0.8 millimeters to 1.2 millimeters inclusively.

8. The dental curing apparatus of claim 7, further comprising: at least one plate securement member configured to removably secure the perforated plate between the light source and the dental composite.

9. The dental curing apparatus of claim 8, wherein the at least one plate securement member comprises two inwardly biased springs positioned along opposite sides of the perforated plate.

10. The dental curing apparatus of claim 7, further comprising: a plate placement member connected to the perforated plate.

11. The dental curing apparatus of claim 7, wherein the plurality of perforations comprises a plurality of evenly spaced and circular-shaped through-holes.

12. The dental curing apparatus of claim 11, wherein each of the plurality of through-holes is 1 millimeter in diameter and spatially separated from other through-holes by 1 millimeter.

13. A dental curing system, comprising:
a light source;
a perforated plate; and
a dental composite,
wherein
the light source is configured to produce a curing light beam, and
the perforated plate is positioned between the light source and a dental composite, the perforated plate comprising a plurality of perforations configured to convert the curing light beam into multiple curing light beams before reaching the dental composite, wherein the diameter of perforations is in the range 0.8 millimeters to 1.2 millimeters inclusively, and their distance apart in the range 0.8 millimeters to 1.2 millimeters inclusively, further wherein the perforations are circular-shaped through-holes.

14. The dental curing system of claim 13, further comprising:
at least one plate securement member configured to removably secure the perforated plate between the light source and the dental composite.

15. The dental curing system of claim 14, wherein the at least one plate securement member comprises two inwardly biased springs positioned along opposite sides of the perforated plate.

16. The dental curing system of claim 13, further comprising:
a plate placement member connected to the perforated plate.

17. The dental curing system of claim 13, wherein the plurality of perforations comprises a plurality of evenly spaced and circular-shaped through-holes.

18. The dental curing apparatus of claim 17, wherein each of the plurality of through-holes is 1 millimeter in diameter and spatially separated from other through-holes by 1 millimeter.

19. A dental curing apparatus, comprising:
a light source;
a holder, the holder comprising an upper light source holder portion, an elongated portion, and a bottom rest portion, wherein the elongated portion is located between the light source holder portion and the rest portion; and
a perforated plate, wherein the perforated plate is attached to and held by the elongated portion of the holder such that the holder and perforated plate form a single integral piece,
wherein the diameter of the perforations is in the range 0.8 millimeters to 1.2 millimeters inclusively, and their distance apart in the range 0.8 millimeters to 1.2 millimeters inclusively,
wherein the light source is configured to produce a curing light beam.

20. The dental curing apparatus of claim 19, wherein each of the plurality of through-holes is 1 millimeter in diameter and spatially separated from other through-holes by 1 millimeter.

* * * * *